(12) United States Patent
Hebert

(10) Patent No.: US 6,919,088 B2
(45) Date of Patent: Jul. 19, 2005

(54) WATER-SOLUBLE STABLE SALTS OF PETROSELINIC ACID

(76) Inventor: Rolland F. Hebert, 427 Bellevue Ave. E. #301, Seattle, WA (US) 98102

( * ) Notice: Subject to any disclaimer, the term of this patent is extended or adjusted under 35 U.S.C. 154(b) by 134 days.

(21) Appl. No.: 10/455,103

(22) Filed: Jun. 5, 2003

(65) Prior Publication Data

US 2003/0228378 A1 Dec. 11, 2003

Related U.S. Application Data

(60) Provisional application No. 60/386,128, filed on Jun. 5, 2002.

(51) Int. Cl.$^7$ ............................ A61K 7/00; A61K 9/00; A61K 31/715; A61K 31/20
(52) U.S. Cl. ........................ 424/401; 424/400; 514/59; 514/558
(58) Field of Search ................................ 424/400, 401; 514/558, 59

(56) References Cited

U.S. PATENT DOCUMENTS

| | | | | |
|---|---|---|---|---|
| 3,697,644 A | * | 10/1972 | Laiderman | ................. 424/70.1 |
| 5,380,359 A | * | 1/1995 | Honda et al. | ................. 106/414 |
| 6,022,896 A | | 2/2000 | Weinkauf et al. | |
| 6,042,841 A | | 3/2000 | Alaluf et al. | |
| 6,190,679 B1 | * | 2/2001 | Takekoshi et al. | ............ 424/401 |
| 6,365,175 B1 | | 4/2002 | Alaluf et al. | |

* cited by examiner

Primary Examiner—Gary Kunz
Assistant Examiner—Marina Lamm

(57) ABSTRACT

Stable water-soluble salts of petroselinic acid with dextran useful as active constituents in pharmaceutical as well as cosmeceutical applications are described.

5 Claims, No Drawings

US 6,919,088 B2

WATER-SOLUBLE STABLE SALTS OF PETROSELINIC ACID

BACKGROUND CROSS-REFERENCES TO RELATED APPLICATION

This application claims the benefit of Provisional Patent Application Ser. No. 60/386,128 filed on Jun. 5, 2002.

FIELD OF THE INVENTION

The present invention relates to new water-soluble stable salts of petroselinic acid with dextran.

TECHNICAL FIELD

This patent relates to new stable salts of petroselinic acid with dextran, the processes for obtaining them and to therapeutic uses of these new salts. More particularly, the invention relates to salts deriving from the reaction between petroselinic acid and dextran, their production process, and pharmaceutical compositions that contain them as active principles.

BACKGROUND OF THE INVENTION

Petroselinic acid (cis-6-octadecenoic acid) is a monounsaturated long chain (C18) fatty acid and is found in relatively high concentrations in coriander and parsley seed oil. In common with other vegetable oils, and especially with the cis configuration which is more unstable than trans, petroselinic acid is oxidatively unstable (resulting in a rancid taste and smell) and must be stored at low temperature. Petroselinic acid has important biological functions that make it an interesting and important molecule from a pharmacological viewpoint.

In vitro, petroselinic acid has been shown to be a competitive inhibitor of topoisomerases. (J Enzyme Inhib 2000; 15(4):357–66. Petroselinic Inhibition of topoisomerases by fatty acids. Suzuki K, Shono F, Kai H, Uno T, Uyeda M) and thus useful in the treatment of cancer. DNA topoisomerases are key enzymes in the interconversion of isomers of DNA molecules. Topoisomerases are involved in many important cell processes such as replication, transcription, and integration.

The topoisomerases are important cellular targets for a number of successful chemotherapeutic agents (Wang, Ann. Rev. Biochem, 65, 635–692, 1996) and are essential enzymes in the regulation of DNA topology which is required if cells are to divide and proliferate (Wang, loc cit). Drugs that target topoisomerase II, for example doxorubicin and etoposide, have been widely used in cancer chemotherapy (Hande, Biophys. Acta 1400, 173–184, 1998) while those that specifically target topoisomerase I, principally the camptothecin analogues, have made an important impact more recently, an example being CPT-11 for the treatment of colon cancer (Dancey et al, Br. J. Cancer 74, 327–338, 1996). More recently, topoisomerases have been shown to be therapeutic targets for antifungal, antibacterial and antiviral drugs (Chen et al, Rev. Pharmacol. Toxicol, 34, 191–218, 1994), and consequently may prove useful as antifungal, antibacterial or antiviral drugs.

In addition to those compounds that specifically target topoisomerase I or II, several joint inhibitors of topoisomerase I and II have been identified and may also be beneficial in the treatment of solid tumors. These compounds include intoplicine (Riou et al, Cancer Res. 53, 5987–5993, 1993), DACA/XR5000 (Finlay et al, Eur. J. Cancer 32A, 708–714, 1996) and TAS-103 (Utsugi et al, J. Cancer Res, 88, 992–1002 1997) which are all in clinical evaluation. The advantage of joint inhibitors of topoisomerase I and II is their ability to avoid drug resistance and to target two key enzymes that affect the topology of DNA which are active at different points in the cell cycle. Inhibition of these enzymes is an important goal in medicinal chemistry since such inhibitors have been shown to be anticancer, antimicrobial as well as antiparasitic drug candidates.

Petroselinic acid has also been shown to have anti-inflammatory properties. Petroselinic acid has been shown to reduce the levels of arachadonic acid, a proinflammatory compound, in tissue lipids of rats. (J Nutr 1995 June;125 (6):1563-8. Petroselinic acid from dietary triacylglycerols reduces the concentration of arachidonic acid in tissue lipids of rats. Weber N, Richter K D, Schulte E, Mukherjee K D.) Alaluf, et al. in U.S. Pat. No. 6,365,175, Apr. 2, 2002 disclose the use of petroselinic acid to inhibit the production of metabolites of arachidonic acid and/or reduce the formation of intracellular adhesion molecules (ICAM) both mechanisms important in the antiinflammatory action of petroselinic acid, but do not disclose the use of stable salts of petroselinic acid with dextran.

Intercellular adhesion molecule is a cell surface protein whose expression is induced by inflammatory mediators. ICAM is required for adhesion of leukocytes to endothelial cells and for several immunological functions including antigen presentation, immunoglobulin production and cytotoxic cell activity. Blocking ICAM function prevents immune cell recognition and activity during transplant rejection and in animal models of rheumatoid arthritis, asthma and reperfusion injury.

Cell-cell adhesion plays a pivotal role in inflammatory and immune responses (Springer et al., 1987 Ann. Rev. Immunol. 5, 223–252). Cell adhesion is required for leukocytes to bind to and migrate through vascular endothelial cells. In addition, cell-cell adhesion is required for antigen presentation to T cells, for B cell induction by T cells, as well as for the cytotoxicity activity of T cells, NK cells, monocytes or granulocytes. Intercellular adhesion molecule-1 (ICAM) is a 110 kilodalton member of the immunoglobulin superfamily that is involved in all of these cell-cell interactions (Simmons et al., 1988 Nature (London) 331, 624–627).

ICAM is expressed on only a limited number of cells and at low levels in the absence of stimulation (Dustin et al., 1986 J. Immunol. 137, 245–254). Upon treatment with a number of inflammatory mediators (lipopolysaccharide, .gamma.-interferon, tumor necrosis factor-.alpha., or interleukin-1), a variety of cell types (endothelial, epithelial, fibroblastic and hematopoietic cells) in a variety of tissues express high levels of ICAM on their surface (Sringer et. al. supra; Dustin et al., supra; and Rothlein et al., 1988 J. Immunol. 141, 1665–1669). Induction occurs via increased transcription of ICAM mRNA (Simmons et al., supra). Elevated expression is detectable after 4 hours and peaks after 16–24 hours of induction.

ICAM induction is critical for a number of inflammatory and immune responses. In vitro, antibodies to ICAM block adhesion of leukocytes to cytokine-activated endothelial cells (Boyd, 1988 Proc. Natl. Acad. Sci. USA 85, 3095–3099; Dustin and Springer, 1988 J. Cell Biol. 107, 321–331). Thus, ICAM expression may be required for the extravasation of immune cells to sites of inflammation. Antibodies to ICAM also block T cell killing, mixed lymphocyte reactions, and T dell-mediated B cell differentiation, suggesting that ICAM is required for these cognate cell interactions (Boyd et al;, supra). The importance of ICAM in antigen presentation is underscored by the inability of ICAM defective murine B cell mutants to stimulate antigen-dependent T cell proliferation (Dang et al., 1990 J. Immunol. 144, 4082–4091). Conversely, murine L cells require transfection with human ICAM in addition to HLA-DR in order to present antigen to human T cells (Altmann et al., 1989 Nature (London) 338, 512–514). In summary, evidence in vitro indicates that ICAM is required for cell-cell interactions critical to inflammatory responses, cellular immune responses, and humoral antibody responses.

Alaluf, et al. U.S. Pat. No. 6,042,841, Mar. 28, 2000, have shown petroselinic acid to be more effective than retinoic acid in combating photoaging of the skin (by upregulating and increasing synthesis of decorin and procollagen-I in in vitro testing compared to retinoic acid). They also showed that petroselinic acid has skin lightening properties. However, Alaluf et al do not disclose the use of stable salts of petroselinic acid with dextran.

Palanker et al in U.S. Pat. No. 6,022,896, Feb. 8, 2000, disclose the use of petroselinic acid in a composition and in a method for reducing or eliminating skin irritation or sting induced by alpha hydroxy acids but do not disclose the use of salts of petroselinic acid with dextran.

Administration of new petroselinic acid compositions of the present invention would have significant utility over a wide range of disorders or conditions. Petroselinic acid is inherently unstable and must be stored at low temperatures. However, despite these precautions, petroselinic acid is still unstable and new methodologies are needed to stabilize the molecule.

Accordingly, there is need in the art for new compositions of petroselinic acid as well as methods related to the use of such compositions. There is need in the art for new stable water-soluble petroselinic acid compositions to treat conditions related to the mechanisms of action of petroselinic acid. There is need in the art for new stable petroselinic acid compositions and for synthetic routes to make such new compositions.

In an attempt to overcome these problems, the inventor has surprisingly discovered that water-soluble petroselinic acid derivatives synthesized as a result of the chemical reaction between salts of petroselinic acid and dextran as described following are stable over a long period of time, are easily synthesized and are economical to produce.

SUMMARY OF THE INVENTION

Briefly stated, the present invention discloses stable water soluble pharmaceutically acceptable salts of petroselinic acid with dextran. In the context of this invention, petroselinic acid refers to both naturally occurring petroselinic acid as well as synthetic petroselinic acid. Dextran is a polysaccharide produced by bacteria growing on sucrose. Natural dextran usually has a high molecular weight. Lower weight dextrans are produced by depolymerization of natural dextran or by synthesis. All dextrans are chemically comprised of alpha-d-glucophyranosyl units. Therapeutically, dextrans are used as plasma volume expanders and are routinely used in medicine. Any type or form of dextran is contemplated in this invention. Petroselinic acid and dextran are commercially available from Sigma-Aldrich Co., St. Louis, Mo.

The water soluble stable petroselinic acid derivatives with dextran of the present invention have utility as antiinflammatory agents in view of their ability to inhibit the production of metabolites of arachidonic acid and/or reduce the formation of intracellular adhesion molecules both of which are important in the inflammatory process. Therefore, a water soluble stable petroselinic acid derivative with dextran would have utility as an antiinflammatory in conditions in which inflammation is a hallmark. Daily dosages of the stable water-soluble petroselinic acid derivatives with dextran can vary within wide limits and will be adjusted to the individual requirements in each particular case. In general, for administration to adults, an appropriate daily dosage is in the range of about 5 mg to about 3000 mg, although the upper limit may be exceeded if expedient. The daily dosage can be administered as a single dosage or in divided dosages.

In another embodiment, a water soluble stable petroselinic acid is used to prevent aging of the skin. Topical application of a water soluble stable petroselinic acid with dextran is applied to the skin to counter the effects of ageing. Preferably the concentration of water soluble stable petroselinic acid with dextran is 5–80% by weight in a dermatologically/cosmetically acceptable vehicle that can be applied to the skin to achieve the desired effect. More preferably, the concentration of water soluble stable petroselinic acid with dextran is 8–30% by weight in a dermatologically/cosmetically acceptable vehicle. Most preferably the water soluble stable petroselinic acid with dextran is 10–20% by weight in a dermatologically/cosmetically acceptable vehicle that can be applied to the skin to achieve the desired effect. However, the preferred concentration of water soluble stable petroselinic acid with dextran is that concentration which is most economic but achieves the desired effect.

In yet another embodiment, a water soluble stable petroselinic acid is used to lighten the color of the skin. Topical application of a water soluble stable petroselinic acid with dextran is applied to the skin to lighten its color. Preferably the concentration of water soluble stable petroselinic acid with dextran is 5–80% by weight in a dermatologically/cosmetically acceptable vehicle that can be applied to the skin to achieve the desired effect. More preferably, the concentration of water soluble stable petroselinic acid with dextran is 8–30% by weight in a dermatologically/cosmetically acceptable vehicle. Most preferably the water soluble stable petroselinic acid with dextran is 10–20% by weight in a dermatologically/cosmetically acceptable vehicle that can be applied to the skin to achieve the desired effect. However, the preferred concentration of water soluble stable petroselinic acid with dextran is that concentration which is most economic but achieves the desired effect.

To prepare the topical composition used in two of the methods of the present invention, the usual manner for preparing skin care products may be employed. The active components are generally incorporated in a dermatologically acceptable carrier in conventional manner. The active components can suitably first be dissolved or dispersed in a portion of the water or another solvent or liquid to be incorporated in the composition.

The composition may be in the form of conventional skin-care products such as a cream, gel or lotion or the like. The composition can also be in the form of a so-called "wash-off" product e.g. a bath or shower gel, possibly containing a delivery system for the actives to promote adherence to the skin during rinsing. Most preferably the product is a "leave-on" product; a product to be applied to the skin without a deliberate rinsing step soon after its application to the skin.

This method of the present invention may be carried out one or more times daily to the skin which requires treatment.

The improvement in skin appearance will usually become visible after 3 to 6 months, depending on skin condition, the concentration of the active components used in the inventive method, the amount of composition used and the frequency with which it is applied. In general, a small quantity of the composition, for example from 0.1 to 5 ml is applied to the skin from a suitable container or applicator and spread over and/or rubbed into the skin using the hands or fingers or a suitable device.

In still a further embodiment, a synthetic method for the manufacture of a stable water soluble petroselinic acid derivative with dextran is disclosed.

In another embodiment, a water soluble stable petroselinic acid derivative with dextran is used to inhibit topoisomerases associated with cancer. Daily dosages of the stable water-soluble petroselinic acid derivatives with dextran can vary within wide limits and will be adjusted to the individual requirements in each particular case. In general, for administration to adults, an appropriate daily dosage is in the range of about 5 mg to about 3000 mg, although the upper limit may be exceeded if expedient. The daily dosage can be administered as a single dosage or in divided dosages.

Other aspects of the present invention will become evident upon reference to the detailed description.

DETAILED DESCRIPTION OF THE INVENTION

As mentioned above, this invention is generally directed to new, stable water-soluble petroselinic acid derivatives with dextran and to methods of their use in the treatment of ageing skin, inflammatory conditions and in cancer. As used herein, the term "conditions" includes diseases, injuries, disorders, indications and/or afflictions that are associated with inflammation, ageing of the skin and increased topoisomerase activity. The term "treat" or "treatment" means that the symptoms associated with one or more conditions associated with inflammation, ageing of the skin and increased topoisomerase activity are alleviated or reduced in severity or frequency, and the term "prevent" means that subsequent occurrence of such symptoms are avoided or that the frequency between such occurrences is prolonged.

In one embodiment of this invention, synthetic routes for the manufacture of stable water soluble petroselinic acid derivatives with dextran are disclosed. In this regard, highly pure stable water soluble petroselinic acid derivatives with dextran can be manufactured in high yield by mixing salt of petroselinic acid with dextran. While sodium salts of petroselinic acid are generally preferred, this patent envisions other salts to be used with petroselinic acid, such as potassium or any other pharmaceutically acceptable salt of petroselinic acid. Generally this synthesis may be achieved by dissolving dextran in water and then adding sodium salt of petroselinic acid with constant stirring at 21 degrees C. for 10 minutes. The solution is dried by freeze drying and results in a stable powder. Any other method for drying may be used but lyophilization is the preferred method.

In another manner of this present embodiment, dextran (and equal in weight to the amount of sodium salt of petroselinic acid that will be added later) is dissolved in water at room temperature. Sodium salt of petroselinic acid (equal in weight to the dextran) is added to this solution with constant stirring for 30 minutes at 21 degrees C. and pH 2.46. The solution is dried by freeze drying and results in a stable powder.

Another method for the synthesis of stabilized petroselinic acid consists of dissolving dextran (average molecular weight 15,000) (one half the amount of the weight of petroselinic acid to be added for stabilization) in water at pH 5.2 and 21 degrees C. Sodium salt of petroselinic acid (twice the amount of dextran) is added to this solution with constant stirring for 30 minutes at 21 degrees C. and pH 2.62. The solution is dried by freeze drying and results in a stable powder. In a more preferable embodiment, the synthesis is carried out in the following manner that lends itself easily to scale up on an industrial level. Dextran (2 grams, average molecular weight 15,000) is dissolved in water (100 ml) at pH 5.2 and 21 degrees C. Sodium salt of petroselinic acid (2 grams) is added to this solution with constant stirring for 30 minutes at 21 degrees C. and pH 2.46. The solution is dried by freeze drying and results in a stable powder.

In an even more preferable embodiment, the synthesis is carried out in the following manner that also lends itself easily to scale up on an industrial level. Dextran (1 gram, average molecular weight 15,000) is dissolved in water (100 ml) at pH 5.2 and 21 degrees C. Petroselinic acid (2 grams) is added to this solution with constant stirring for 30 minutes at 21 degrees C. and pH 2.62. The solution is dried by freeze drying and results in a stable powder. (Drying may of course also be carried out by other methods than freeze drying and that are all well known in the art.) The amount of dextran that may be used to stabilize petroselinic acid in the synthetic process of this present invention can range from 1% of the weight of petroselinic acid to be stabilized to 100% of the weight of the petroselinic acid. For reasons of economy, the least amount of dextran needed to stabilize the petroselinic acid is the preferred quantity. The pH of the dextran solutions in which the petroselinic acid is dissolved may range from pH 1 to pH 6.9 but more preferably from pH2.3–pH3.5.

The water soluble petroselinic acid derivatives with dextran of this invention may be used to prevent and/or treat a variety of conditions associated with inflammation. To this end, the water soluble petroselinic acid derivatives with dextran of the present invention may be used for pharmaceutical, prophylactic and/or cosmetic purposes, and are administered to a warmblooded animal in an effective amount to achieve a desired result. In the case of pharmaceutical administration, an effective amount is a quantity sufficient to treat the symptoms of a condition and/or the underlying condition itself. An effective amount in the context of prophylactic administration means an amount sufficient to avoid or delay the onset of a condition and/or its symptoms.

Lastly, an effective amount with regard to cosmetic administration is an amount sufficient to achieve the desired cosmetic result.

In a preferred embodiment, the water soluble petroselinic acid derivatives with dextran of the present invention are administered to a warm-blooded animal as a pharmaceutical, prophylactic or cosmetic composition. Administration may be accomplished by systemic or topical application, with the preferred mode dependent upon the type and location of the conditions to be treated. Frequency of administration may vary, and is typically accomplished by daily administration.

Systemic administration may be achieved, for example, by injection (e.g., intramuscular, intravenous, subcutaneous or intradermal) or oral delivery of the composition to the warm-blooded animal. Suitable carriers and diluents for injection are known to those skilled in the art, and generally are in the form of an aqueous solution containing appropriate buffers and preservatives. Oral delivery is generally accomplished by formulating the composition in a liquid or solid form, such as a tablet or capsule, by known formulation techniques. Daily dosages of compositions of the present invention may vary depending on the condition of the patient, the patient's health history and other medications, and the like. In general, dosages of compositions of the present invention are administered to mammals in need thereof at dosage levels of approximately 5 mg to 20 grams per day, and more preferably at dosage levels of approximately 100 mg to 3 grams per day. Treatment protocols may involve a single daily dosage, or may involve equally divided doses throughout the day.

Topical administration may be accomplished, for example, by formulating the composition as solution, cream, gel, ointment, powder, paste, gum or lozenge using techniques known to those skilled in the formulation field. As used herein, topical administration includes delivery of the composition to mucosal tissue of the mouth, nose and throat by, for example, spray or mist application, as well as to the vagina and rectum by, for example, suppository application.

It has now surprisingly and unexpectedly been found that stable pharmaceutically acceptable salts of petroselinic acid with dextran have good characteristics that are such as to render them particularly suitable both for use in pharmaceutical formulations and for preparative applications. Owing to their simple conception and low costs, the procedures described in this invention easily lend themselves to working out methods of preparation on an industrial scale.

The example given herein below illustrates the preparation of a stable petroselinic acid salt with dextran. Only one of the many possible embodiments that may be anticipated are shown by this example that is intended to define, in a non-limiting sense, the scope encompassed by the invention.

This example is given to illustrate the present invention, but not by way of limitation. Accordingly, the scope of this invention should be determined not by the embodiment illustrated, but rather by the appended claims and their legal equivalents.

EXAMPLE 1

Dextran (0.10 grams) was dissolved in water (3 ml) and dissolved completely. The sodium salt of petroselinic acid (0.1 gram) was added to the solution and stirred at room temperature for 10 minutes. The solution was filtered and dried by lyophylization. The resulting powder was stored in a vial at room temperature for over one year without evidence of rancid smell or taste. (Smell and taste are acceptable indicators of rancidity.)

What is claimed is:

1. An anti-inflammatory composition comprising an effective amount of a stable powdered conjugate of petroselinic acid or a pharmaceutically acceptable salt thereof and dextran, wherein said conjugate is produced by the method comprising: (1) dissolving an effective amount of dextran in water; (2) adding an effective amount of petroselinic acid or a pharmaceutically acceptable salt thereof to the dextran solution at a pH ranging from 1 to 3.5; (3) stirring the solution; (4) lyophilizing the resultant solution to produce a stable powder.

2. The composition of claim 1 wherein the solution is stirred for 30 minutes at 21 degrees C.

3. The composition of claim 1 wherein the amount of dextran is between 0.1%–100% of the weight of the petroselinic acid or a pharmaceutically acceptable salt thereof.

4. The composition of claim 1 wherein the amount of dextran is between 10%–80% of the weight of the petroselinic acid or a pharmaceutically acceptable salt thereof.

5. The composition of claim 1 wherein the amount of dextran is between 30%–60% of the weight of the petroselinic acid or a pharmaceutically acceptable salt thereof.

* * * * *